US012563650B2

(12) United States Patent
Maa et al.

(10) Patent No.: US 12,563,650 B2
(45) Date of Patent: Feb. 24, 2026

(54) GAMMA STIMULATION APPARATUS

(71) Applicant: Aleddra Inc., Renton, WA (US)

(72) Inventors: Chia-Yiu Maa, Bellevue, WA (US);
Chun-Te Yu, Bellevue, WA (US)

(73) Assignee: Aleddra Inc., Renton, WA (US)

( * ) Notice: Subject to any disclaimer, the term of this
patent is extended or adjusted under 35
U.S.C. 154(b) by 105 days.

(21) Appl. No.: 18/802,264

(22) Filed: Aug. 13, 2024

(65) Prior Publication Data

US 2025/0227832 A1 Jul. 10, 2025

Related U.S. Application Data

(63) Continuation-in-part of application No. 18/626,148,
filed on Apr. 3, 2024, which is a continuation-in-part
(Continued)

(51) Int. Cl.
*H05B 45/32* (2020.01)
*A61M 21/00* (2006.01)
*H05B 45/37* (2020.01)

(52) U.S. Cl.
CPC ............. *H05B 45/32* (2020.01); *A61M 21/00*
(2013.01); *H05B 45/37* (2020.01); *A61M*
*2021/0044* (2013.01)

(58) Field of Classification Search
CPC .... H05B 45/37; H05B 45/10; H05B 45/3725;
H05B 45/48; H05B 45/14; H05B 45/44;
H05B 45/40; H05B 47/10; H05B 45/42;
H05B 39/04; H05B 39/044; H05B
39/048; H05B 45/38; H05B 45/20; H05B
45/375; H05B 45/36; H05B 47/19; H05B
41/3924; H05B 45/46; H05B 33/02;

H05B 47/155; H05B 45/31; H05B
45/315; H05B 45/385; H05B 45/59;
H05B 45/35; H05B 45/39; H05B 45/50;
H05B 45/00; H05B 45/395; H05B 41/28;
H05B 45/3575; H05B 45/3578; H05B
45/327; H05B 45/355; H05B 45/305;
H05B 45/325; H05B 47/185; H05B
33/12; H05B 33/14; H05B 41/282; H05B
41/2928; H05B 45/54; H05B 41/2828;
H05B 44/00; H05B 45/397; H05B 45/58;
H05B 45/357; H05B 45/3574; H05B
45/382; H05B 41/16; H05B 41/24; H05B
41/2821; H05B 41/2827; H05B 45/345;
(Continued)

(56) References Cited

U.S. PATENT DOCUMENTS

2022/0036793 A1* 2/2022 Petluri .................. H05B 47/17

* cited by examiner

*Primary Examiner* — Monica C King
(74) *Attorney, Agent, or Firm* — Andy M. Han; Han IP
PLLC

(57) ABSTRACT

A gamma stimulation apparatus comprises a rectifier, a
control module, a first modulation operation switch (MOS),
a second MOS, and first and second light sources. The
control module operates the first light source at a first
operating frequency (OF1) via the first MOS, and the second
light source at a second frequency (OF2) via the second
MOS. The first and second light outputs superimpose each
other to form a superimposed light having a superimposed
frequency equal to OF2–OF1 and between 20 Hz and 45 Hz.
For every fixed period of a recalibration cycle, the control
module is configured to operate only one of the two light
sources or operate two light sources at a same frequency.

24 Claims, 4 Drawing Sheets

Related U.S. Application Data of application No. 18/613,079, filed on Mar. 21, 2024, which is a continuation-in-part of application No. 18/408,523, filed on Jan. 9, 2024.

(58) Field of Classification Search
CPC .. H05B 47/105; H05B 47/16; H05B 41/2822; H05B 41/3927; H05B 45/18; H05B 45/30; H05B 45/32; H05B 47/196; H05B 47/1985; H05B 41/2856; H05B 41/295; H05B 41/2986; H05B 41/3925; H05B 45/34; H05B 47/115; H05B 47/14; H05B 47/165; H05B 39/085; H05B 41/2888; H05B 41/2923; H05B 41/3928; H05B 47/17; H05B 47/175; H05B 47/18; H05B 47/184; H05B 47/1965; H05B 47/198; H05B 47/20; H05B 47/21; H05B 47/24; H05B 47/25; H05B 47/26
See application file for complete search history.

GAMMA STIMULATION APPARATUS

CROSS REFERENCE TO RELATED PATENT APPLICATIONS

The present disclosure is a continuation-in-part (CIP) of U.S. patent application Ser. No. 18/626,148, filed 3 Apr. 2024, which itself is a CIP of U.S. patent application Ser. No. 18/613,079, filed 21 Mar. 2024, which is itself is a CIP of U.S. patent application Ser. No. 18/408,523, filed 9 Jan. 2024. Contents of aforementioned applications are herein incorporated by reference in their entirety.

BACKGROUND

Technical Field

The present disclosure pertains to the field of lighting apparatus and, more specifically, proposes gamma stimulation apparatus.

Description of Related Art

It has been discovered that by flickering a light at a frequency between 35 Hz and 45 Hz or generating a sound at a similar frequency has the effect of stimulating the cells in certain region of the brain, resulting in using a flicking light or a sound at such a frequency for treating Alzheimer's disease. However, turning on and off a light source at a frequency between 35 Hz and 45 Hz can create visual discomfort to the eyes of a subject. Different approaches have been introduced to overcome this visual discomfort under 40 Hz flickering light.

U.S. patent application Ser. No. 18/626,148 introduces a gamma stimulation apparatus comprises a rectifier, a control module, a first modulation operation switch (MOS), a second MOS, and first and second light sources. The control module sends the first MOS a first signal having a first periodical waveform at a first operating frequency (OF1). The first MOS operates the first light source according to the first signal, producing a first light output at the OF1 frequency. The control module sends the second MOS a second signal having a second periodical waveform at a second operating frequency (OF2). The second MOS operates the second light source according to the second signal, producing a second light output at the OF2 frequency. The first and second light outputs superimpose each other to form a superimposed light having a superimposed frequency equal to OF2–OF1 and between 20 Hz and 45 Hz. The superimposed light appears flicker-free (free of flicker) to eyes of a subject.

In U.S. patent application Ser. No. 18/408,523, a recalibration cycle was introduced during which only one of the two light sources would operate at a fixed frequency for a short period of time. The benefit of having a recalibration cycle is that it allows the brain of a subject to phase-lock with the frequency of the operating light source during the mono light source duration, thus enabling a better recognition of the frequency difference when both light sources are operating simultaneously but each at a different frequency, subsequently resulting a more effective treatment for Alzheimer's disease patients. U.S. patent application Ser. No. 18/626,148, however, does not address the recalibration cycle nor specify its implementation.

The present disclosure proposes different means of implementing the recalibration cycle for the gamma stimulation apparatuses introduced in U.S. patent application Ser. No. 18/626,148.

SUMMARY

In one aspect, the gamma stimulation apparatus comprises a rectifier, a control module, a first modulation operation switch (MOS), a second MOS, a first light source, and a second light source. The rectifier is configured to convert an external alternating current (AC) power to an internal direct current (DC) power to power the control module, the first light source, and the second light source. The control module is configured to send the first MOS a first signal having a first periodical waveform at a first operating frequency (OF1), and subsequently, the first MOS (functioning like a switch) is configured to operate the first light source according to the first signal, producing a first light output at the OF1 frequency. Similarly, the control module is configured to send the second MOS a second signal having a second periodical waveform at a second operating frequency (OF2), greater than the OF1 frequency, and subsequently, the second MOS (functioning like a switch) is configured to operate the second light source according to the second signal, producing a second light output at the OF2 frequency. The first light output and the second light output superimpose each other to form a superimposed light having a superimposed frequency equal to OF2–OF1. The superimposed frequency is between 20 Hz and 45 Hz. The superimposed light appears flicker-free (free of flicker) to eyes of a subject. The control module may be implemented via a microcontroller, though it is not required. Moreover, the control module is configured, for every fixed period of a recalibration cycle, to suspend or turn off one of the two light sources for a short period of time of a mono light source duration and to boost a respective light output of the other of the two light sources to maintain a total light output of the apparatus the same as when both light sources are on.

FIG. 1 shows a first periodical (sinusoidal) waveform at 8 Hz and a second periodical (sinusoidal) waveform as 12 Hz, producing a superimposed waveform (in red) at 4 Hz. FIG. 2 shows a first periodical (trapezoidal) waveform at 8 Hz and a second periodical (trapezoidal) waveform as 12 Hz, producing a superimposed waveform (in red) at 4 Hz. FIG. 3 shows two more periodical trapezoidal waveforms with longer ON state, also producing a superimposed waveform (in red) at 4 Hz. The trapezoidal waveforms in FIG. 2 and FIG. 3 can be replaced with rectangular waveforms, square waveforms, or triangular waveforms, and they could also produce corresponding superimposed waveforms at 4 Hz.

In some embodiments, the recalibration cycle is between 1 and 120 minutes. In some embodiments, the mono operating frequency duration is between 5 and 60 seconds.

In another aspect, the gamma stimulation apparatus comprises a rectifier, a control module, a first MOS, a second MOS, a first light source, and a second light source. The rectifier is configured to convert an external AC power to an internal DC power to power the control module, the first light source, and the second light source. The control module is configured to send the first MOS a first signal having a first periodical waveform at a first operating frequency (OF1), and subsequently, the first MOS (functioning like a switch) is configured to operate the first light source according to the first signal, producing a first light output at the OF1 frequency. Similarly, the control module is configured to send the second MOS a second signal having a second periodical waveform at a second operating frequency (OF2), greater than the OF1 frequency, and subsequently, the second MOS (functioning like a switch) is configured to operate the second light source according to the second signal, producing a second light output at the OF2 frequency. The first light output and the second light output superimpose each other to form a superimposed light having a superimposed frequency equal to OF2−OF1. The superimposed frequency is between 20 Hz and 45 Hz. The superimposed light appears flicker-free (free of flicker) to eyes of a subject. The control module may be implemented via a microcontroller, though it is not required. Moreover, the control module is configured, for every fixed period of a recalibration cycle, to set the first signal and the second signal at a same frequency (e.g., either the OF1 frequency or the OF2 frequency) for a short period of time of a mono frequency duration.

In some embodiments, the recalibration cycle is between 1 and 120 minutes. In some embodiments, the mono operating frequency duration is between 5 and 60 seconds.

It is foreseeable to use two control modules, one for operating the first MOS and the other for operating the second MOS. Thus, in another aspect, the gamma apparatus comprises a rectifier, a first control module, a second control module, a first MOS, a second MOS, a first light source and a second light source. The rectifier is configured to convert an external AC power to an internal DC power to power the first control module, the second control module, the first light source, and the second light source. The first control module is configured to send the first MOS a first signal having a first periodical waveform at a first operating frequency (OF1), and subsequently, the first MOS is configured to operate the first light source according to the first signal, producing a first light output at the OF1 frequency. The second control module is configured to send the second MOS a second signal having a second periodical waveform at a second operating frequency (OF2), greater than the OF1 frequency, and subsequently, the second MOS is configured to operate the second light source according to the second signal, producing a second light output at the OF2 frequency. The first light output and the second light output superimpose each other to form a superimposed light having a superimposed frequency equal to OF2−OF1. The superimposed frequency is between 20 Hz and 45 Hz. The superimposed light appears flicker-free (free of flicker) to eyes of a subject. Moreover, the first control module and the second control module are configured, for every fixed period of a recalibration cycle, to suspend or turn off one of the two light sources for a short period of time of a mono light source duration and to boost a respective light output of the other of the two light sources to maintain a total light output of the apparatus the same as when both light sources are on.

In some embodiments, the recalibration cycle is between 1 and 120 minutes. In some embodiments, the mono operating frequency duration is between 5 and 60 seconds.

In another aspect, the gamma apparatus comprises a rectifier, a first control module, a second control module, a first MOS, a second MOS, a first light source and a second light source. The rectifier is configured to convert an external AC power to an internal DC power to power the first control module, the second control module, the first light source, and the second light source. The first control module is configured to send the first MOS a first signal having a first periodical waveform at a first operating frequency (OF1), and subsequently, the first MOS is configured to operate the first light source according to the first signal, producing a first light output at the OF1 frequency. The second control module is configured to send the second MOS a second signal having a second periodical waveform at a second operating frequency (OF2), greater than the OF1 frequency, and subsequently, the second MOS is configured to operate the second light source according to the second signal, producing a second light output at the OF2 frequency. The first light output and the second light output superimpose each other to form a superimposed light having a superimposed frequency equal to OF2−OF1. The superimposed frequency is between 20 Hz and 45 Hz. The superimposed light appears flicker-free (free of flicker) to eyes of a subject. Moreover, the first control module and the second control module are configured, for every fixed period of a recalibration cycle, to set the first signal and the second signal respectively at a same frequency (e.g., either the OF1 frequency or the OF2 frequency) for a short period of time of a mono frequency duration.

In some embodiments, the recalibration cycle is between 1 and 120 minutes. In some embodiments, the mono operating frequency duration is between 5 and 60 seconds.

In another aspect, the gamma stimulation apparatus comprises a rectifier, a control module, an MOS, and a light source. The rectifier is configured to convert an external AC power to an internal DC power to power the control module and the light source. The control module is configured to send the MOS a signal having a periodical waveform signal at a first frequency (F1) between 20 Hz and 45 Hz, and subsequently, the MOS is configured to operate the light source according to the signal, producing a light output at the F1 frequency. The periodical waveform is decomposable into a first periodical baseline waveform at a second frequency (F2) and a second periodical baseline waveform at a third frequency (F3) such that F1=F3−F2. A light output of the light source appears flicker-free (free of flicker) to eyes of a subject. Moreover, the control module is configured, for every fixed period of a recalibration cycle, to operate the MOS according to either the first periodical baseline waveform at the F2 frequency or the second periodical baseline waveform at the F3 frequency for a short period of time of a mono frequency duration.

In some embodiments, the recalibration cycle is between 1 and 120 minutes. In some embodiments, the mono operating frequency duration is between 5 and 60 seconds.

The control module(s) and the MOS(es) mentioned above may be combined into a control module, whereas the light source(s) stated above may be external, so long as the control module could power the external light source(s) with suitable periodical waveform(s). Thus, in another aspect, a gamma stimulation apparatus comprises a rectifier and a control module having a first power output port and a second power output port. The is configured to convert an external AC power to an internal DC power to power the control module. The control module is configured to output via the first power output port a first output power having a first periodical waveform at a first operating frequency (OF1). The control module is configured to output via the second power output port a second output power having a second periodical waveform at a second operating frequency (OF2). The first power output port is configured to power a first external light source and the second power output port is configured to power a second external light source. A light output of the first external light source and a light output of the second external light source superimpose each other to form a superimposed light having a superimposed frequency equal to OF2−OF1. The superimposed frequency is between 20 Hz and 45 Hz. The superimposed light appears flicker-free (free of flicker) to eyes of a subject. Moreover, the control module is configured, for every fixed period of a recalibration cycle, to suspend or turn off one of the two output powers for a short period of time of a mono light source duration and to boost the other of the two output powers (subsequently boosting the light output of the external light source powered by the other of the two output powers) to maintain a light output the same as when both external light sources are on.

In some embodiments, the recalibration cycle is between 1 and 120 minutes. In some embodiments, the mono operating frequency duration is between 5 and 60 seconds.

The control module(s) and the MOS(es) mentioned above may be combined into a control module, whereas the light source(s) stated above may be external, so long as the control module could power the external light source(s) with suitable periodical waveform(s). Thus, in another aspect, a gamma stimulation apparatus comprises a rectifier and a control module having a first power output port and a second power output port. The is configured to convert an external AC power to an internal DC power to power the control module. The control module is configured to output via the first power output port a first output power having a first periodical waveform at a first operating frequency (OF1). The control module is configured to output via the second power output port a second output power having a second periodical waveform at a second operating frequency (OF2). The first power output port is configured to power a first external light source and the second power output port is configured to power a second external light source. A light output of the first external light source and a light output of the second external light source superimpose each other to form a superimposed light having a superimposed frequency equal to OF2–OF1. The superimposed frequency is between 20 Hz and 45 Hz. The superimposed light appears flicker-free (free of flicker) to eyes of a subject. Moreover, the control module is configured, for every fixed period of a recalibration cycle, to output the first output power and the second output power at a same frequency (e.g., either the OF1 frequency or the OF2 frequency) for a short period of time of a mono frequency duration.

In some embodiments, the recalibration cycle is between 1 and 120 minutes. In some embodiments, the mono operating frequency duration is between 5 and 60 seconds.

In yet another aspect, the gamma stimulation apparatus comprises a rectifier and a control module having a power outport. The rectifier is configured to convert an external AC power to an internal DC power to power the control module. The control module is configured to output via the power output port and output power having a periodical waveform signal at a first frequency (F1) between 20 Hz and 45 Hz. The periodical waveform is decomposable into a first periodical baseline waveform at a second frequency (F2) and a second periodical baseline waveform at a third frequency (F3) such that F1=F3–F2. The power output port is configured to power an external light source. A light output of the external light source appears flicker-free (free of flicker) to the eyes of a subject. Moreover, the control module is configured, for every fixed period of a recalibration cycle, to output the output power according to either first periodical baseline waveform at the F2 frequency or the second periodical baseline waveform at the F3 frequency for a short period of time of a mono frequency duration.

In some embodiments, the recalibration cycle is between 1 and 120 minutes. In some embodiments, the mono operating frequency duration is between 5 and 60 seconds.

BRIEF DESCRIPTION OF THE DRAWINGS

The accompanying drawings are included to aid further understanding of the present disclosure and are incorporated in and constitute a part of the present disclosure. The drawings illustrate a select number of embodiments of the present disclosure and, together with the detailed description below, serve to explain the principles of the present disclosure. It is appreciable that the drawings are not necessarily to scale, as some components may be shown to be out of proportion to size in actual implementation in order to clearly illustrate the concept of the present disclosure.

DETAILED DESCRIPTION OF PREFERRED EMBODIMENTS

Overview

Various implementations of the present disclosure and related inventive concepts are described below. It should be acknowledged, however, that the present disclosure is not limited to any particular manner of implementation, and that the various embodiments discussed explicitly herein are primarily for purposes of illustration. For example, the various concepts discussed herein may be suitably implemented in a variety of gamma stimulation apparatuses having different form factors.

A gamma stimulation apparatus comprises a rectifier, a control module, a first modulation operation switch (MOS), a second MOS, and first and second light sources. The control module operates the first light source at a first operating frequency (OF1) via the first MOS, and the second light source at a second frequency (OF2) via the second MOS. The first and second light outputs superimpose each other to form a superimposed light having a superimposed frequency equal to OF2–OF1 and between 20 Hz and 45 Hz. For every fixed period of a recalibration cycle, the control module is configured to operate only one of the two light sources or operate two light sources at a same frequency.

Example Implementations

Figure 4:
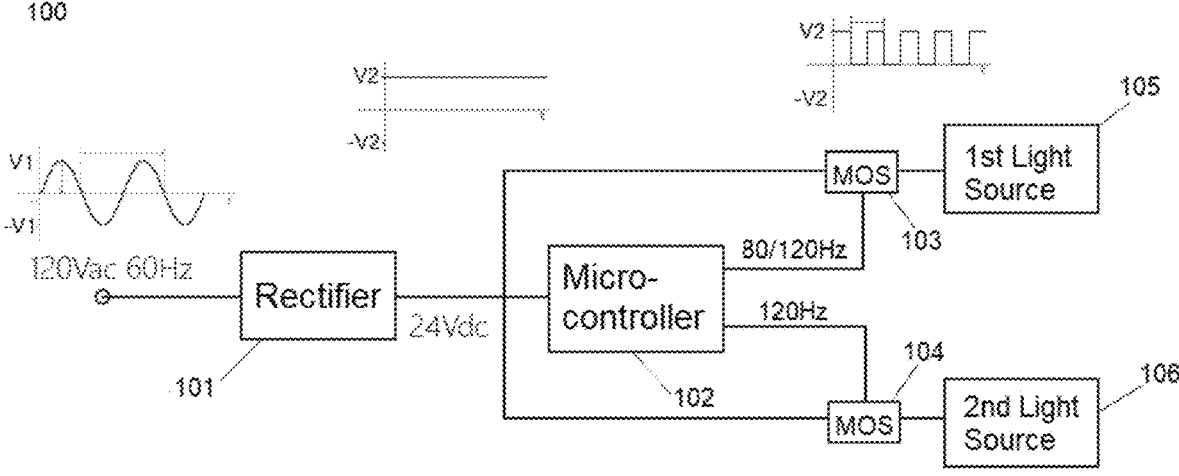
FIG. 4 schematically depicts an embodiment of the present disclosure using one control module and two light sources supporting recalibration cycle with mono frequency duration.

FIG. 4 shows an embodiment of the gamma stimulation apparatus of the present disclosure 100. It comprises a rectifier 101, a microprocessor 102, a first MOS 103, a second MOS 104, a first light source 105, and a second light source 106. The rectifier 101 converts an external AC power (120 Vac at 60 Hz) to an internal DC power (at V2 voltage=24V) to power the microprocessor 102, the first light source 105, and the second light source 106. Embodiment 100 supports a recalibration cycle with mono frequency duration. Microprocessor 102 sends the first MOS 103 a first signal having a first periodical waveform (e.g., a square waveform) at a first operating frequency (OF1) either 80 Hz during normal operation (i.e., outside of the mono frequency duration) or 120 Hz during the mono frequency duration. The first MOS 103 functions like a switch to turn on and off the first light source 105 according to the first signal, producing a first light output at the OF1 frequency either 80 Hz during normal operation or 120 Hz during the mono frequency duration. The recalibration cycle may be set between 1 and 120 minutes. The mono frequency duration may be set tween 5 to 60 seconds. Microprocessor 102 sends the second MOS 104 a second signal having a second periodical waveform (e.g., also a square waveform) at a second operating frequency (OF2) 120 Hz. The second MOS 104 functions like a switch to turn on and off the second light source 106 according to the second signal, producing a second light output at the OF2 frequency 120 Hz. The first light output and the second light output superimpose each other to form a superimposed light having a superimposed frequency. During normal operation (i.e., outside of the mono frequency duration), the OF1 frequency equals 80 Hz, and thus the superimposed frequency equals OF2–OF1=120 Hz–80 Hz=40 Hz. Such superimposed light appears flicker-free (free of flicker) to eyes of a subject. The first periodical waveform and the second periodical waveform may have a same waveform style, i.e., square waveform as shown in FIG. 4, but differ in frequency. During the mono frequency duration, the OF1 frequency equals 120 Hz, so the superimposed frequency equals 120 Hz, and there is no flickering, since human subject can't see any flickering at 120 Hz. The first light source 105 and the second light source 106 comprise an LED or OLED.

In FIG. 4, the first light source 105 and the second light source 106 are shown to operate with square waveforms at V2 voltage=24V. However, it is not required for the first light source 105 and the second light source 106 to operate at the same 24V DC voltage as the microprocessor 102. The present disclosure only requires that the internal DC power to power the microprocessor, the first light source, and the second light source. It is foreseeable to adjust the internal DC power to a different voltage, different from the voltage for powering the microprocessor, to power the first light source and the second light source.

In another embodiment, microprocessor 102 may be modified to support the mono light source duration such that for every recalibration cycle, the first light source is turned off during the mono light source duration and at the same time the light output of the second light source is boosted so as to maintain a total light output of the apparatus the same as when both light sources are on. Under this embodiment, the first light source 105 operates at 80 Hz when it is on.

Figure 5:
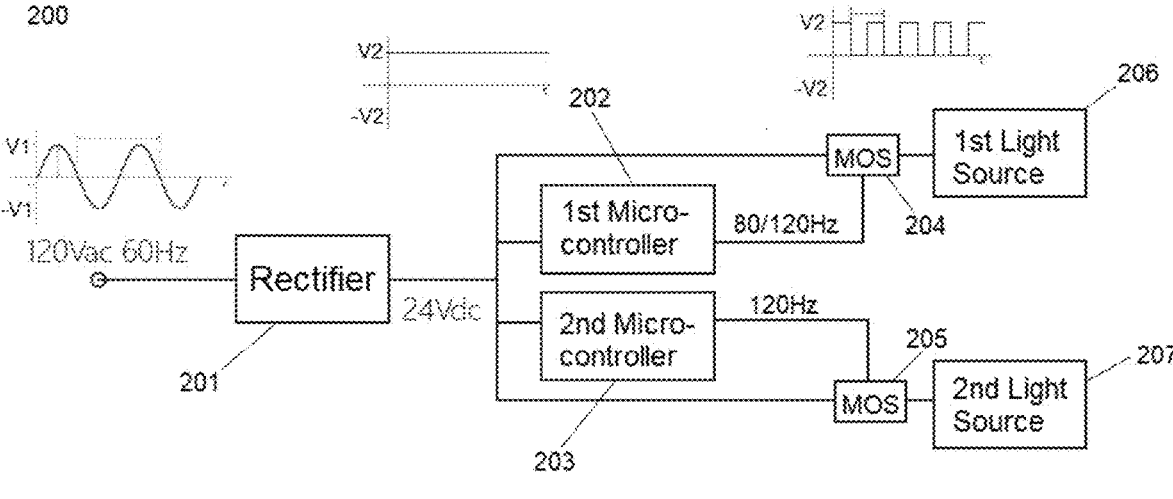
FIG. 5 schematically depicts an embodiment of the present disclosure using two control modules and two light sources supporting recalibration cycle with mono frequency duration.

FIG. 5 shows another embodiment of the gamma stimulation apparatus of the present disclosure 200. It comprises a rectifier 201, a first microprocessor 202, a second microprocessor 203, a first MOS 204, a second MOS 205, a first light source 206, and a second light source 207. The rectifier 201 converts an external AC power (120 Vac at 60 Hz) to an internal DC power (at V2 voltage=24V) to power the first microprocessor 202, the second microprocessor 203, the first light source 206, and the second light source 207. Embodiment 200 supports a recalibration cycle with mono frequency duration. The first microprocessor 202 sends the first MOS 204 a first signal having a first periodical waveform (e.g., a square waveform) at a first operating frequency (OF1) either 80 Hz during normal operation (i.e., outside of the mono frequency duration) or 120 Hz during the mono frequency duration. The first MOS 204 functions like a switch to turn on and off the first light source 206 according to the first signal, producing a first light output at the OF1 frequency either 80 Hz during normal operation or 120 Hz during the mono frequency duration. The recalibration cycle may be set between 1 and 120 minutes. The mono frequency duration may be set tween 5 to 60 seconds. The second microprocessor 203 sends the second MOS 205 a second signal having a second periodical waveform (e.g., also a square waveform) at a second operating frequency (OF2) 120 Hz. The second MOS 205 functions like a switch to turn on and off the second light source 207 according to the second signal, producing a second light output at the OF2 frequency 120 Hz. The first light output and the second light output superimpose each other to form a superimposed light having a superimposed frequency. During normal operation (i.e., outside of the mono frequency duration), the OF1 frequency equals 80 Hz, and thus the superimposed frequency equals OF2–OF1=120 Hz–80 Hz=40 Hz. Such superimposed light appears flicker-free (free of flicker) to eyes of a subject. The first periodical waveform and the second periodical waveform may have a same waveform style, i.e., square waveform as shown in FIG. 5 but differ in frequency. During the mono frequency duration, the OF1 frequency equals 120 Hz, so the superimposed frequency equals 120 Hz, and there is no flickering, since human subject can't see any flickering at 120 Hz. The first light source 206 and the second light source 207 comprise an LED or OLED.

In FIG. 5, the first light source 206 and the second light source 207 are shown to operate with square waveforms at V2 voltage=24V. However, it is not required for the first light source 206 and the second light source 207 to operate at the same 24V DC voltage as the first microprocessor 202 and the second microprocessor 203. The present disclosure only requires the internal DC power to power the first microprocessor, the second microprocessor, the first light source, and the second light source. It is foreseeable to adjust the internal DC power to a different voltage, different from the voltage for powering the first microprocessor and the second microprocessor, to power the first light source and the second light source.

In another embodiment, microprocessors 202 and 203 may be modified to support the mono light source duration such that for every recalibration cycle, the first light source is turned off during the mono light source duration and at the same time the light output of the second light source is boosted so as to maintain a total light output of the apparatus the same as when both light sources are on. Under this embodiment, the first light source 206 operates at 80 Hz when it is on.

Figure 6:
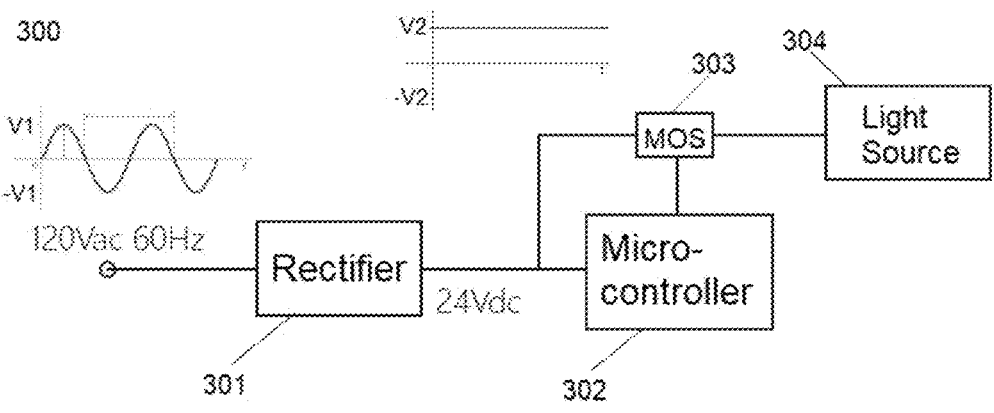
FIG. 6 schematically depicts an embodiment of the present disclosure using one control module and one light source supporting recalibration cycle with mono frequency duration.

FIG. 6 shows another embodiment of the gamma stimulation apparatus of the present disclosure 300. It comprises a rectifier 301, a microprocessor 302, a MOS 303, and a light source 304. The rectifier 301 is configured to convert an external AC power to an internal DC power (at V2 voltage=24V) to power the microprocessor 302 and the light source 304. Embodiment 300 supports a recalibration cycle with mono frequency duration. The recalibration cycle may be set between 1 and 120 minutes. The mono frequency duration may be set tween 5 to 60 seconds. During normal operation (i.e., outside of the mono frequency duration), microprocessor 302 sends the MOS 303 a signal having a periodical waveform signal at a first frequency (F1) 40 Hz (like the superimposed waveform in FIG. 1 but at 40 Hz). The MOS 303 functions like a switch to turn on and off the light source 304 according to the signal, producing a light output at the F1 frequency 40 Hz. The periodical waveform is decomposable into a first periodical baseline waveform at a second frequency (F2) 80 Hz (like the first waveform in FIG. 1 but at 80 Hz) and a second periodical baseline waveform at a third frequency (F3) 120 Hz (like the second waveform in FIG. 1 but at 120 Hz) such that F1=F3–F2=120 Hz–80 Hz=40 Hz. A light output of the light source 304 appears flicker-free (free of flicker) to eyes of a subject. Then during the mono frequency duration, microprocessor 302 sends the MOS 303 a signal having the second periodical baseline waveform at the F3 frequency.

In FIG. 6, the light source 304 may or may not operate at V2 voltage=24V, the voltage used for powering the micro-processor 302. The present disclosure only requires that the internal DC power to power the microprocessor and the light source. It is foreseeable to adjust the internal DC power to a different voltage, different than the voltage for powering the microprocessor, to power the light source.

Figure 1:
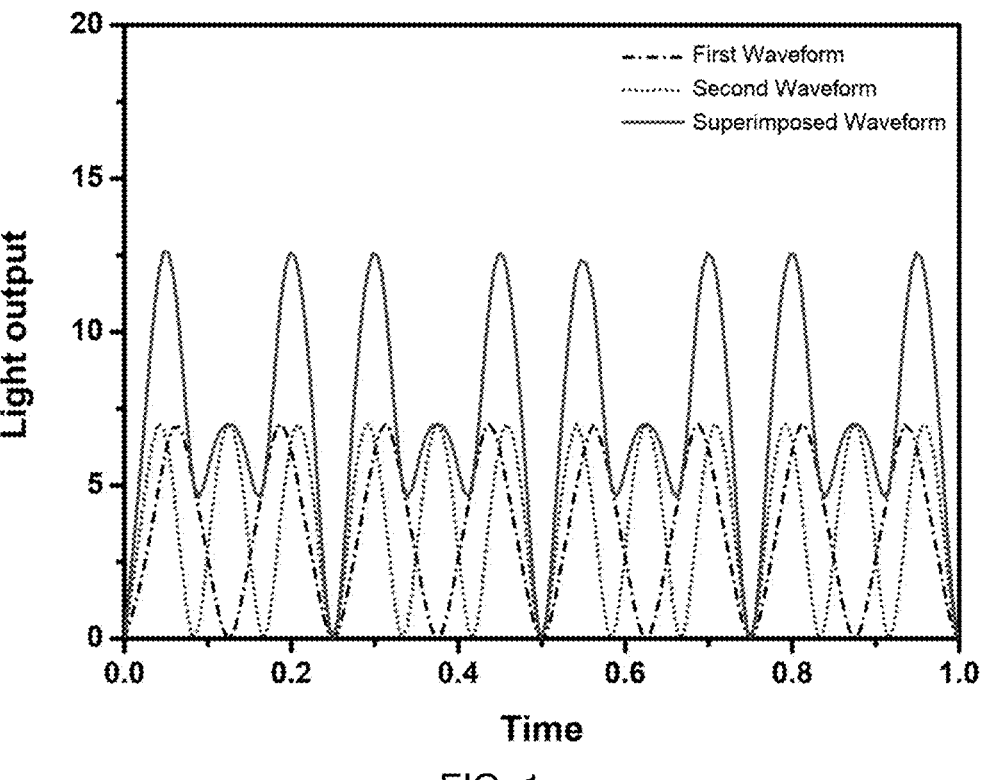
FIG. 1 schematically depicts the superimposing of two sinusoidal waveforms with a first periodical waveform at 8 Hz and the second periodical waveform at 12 Hz.
Figure 2:
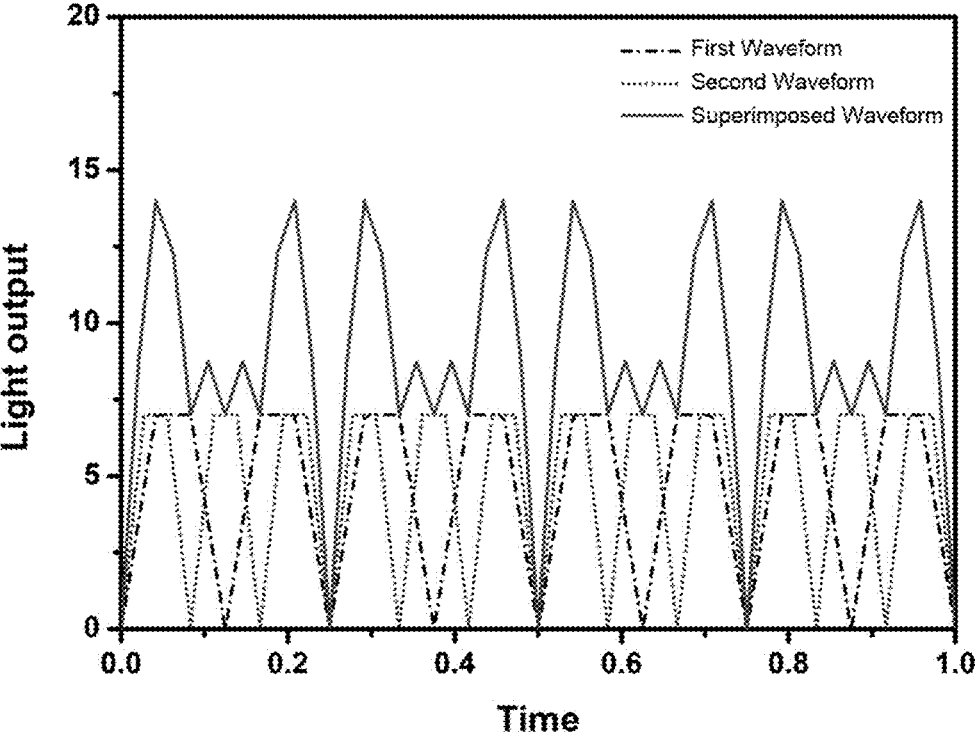
FIG. 2 schematically depicts the superimposing of two trapezoidal waveforms with a first periodical waveform at 8 Hz and the second periodical waveform at 12 Hz.
Figure 3:
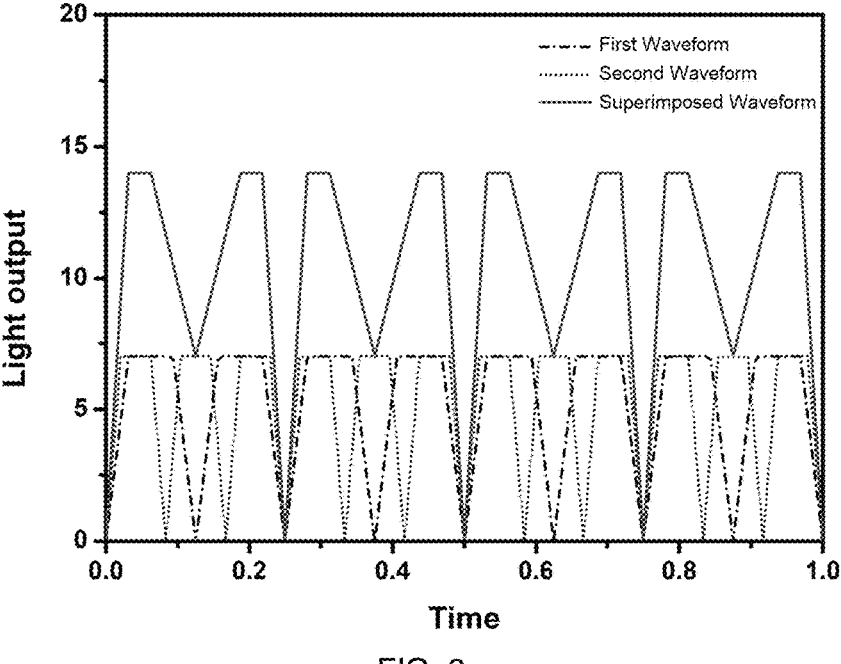
FIG. 3 schematically depicts the superimposing of two more trapezoidal waveforms with longer On-state duration.

During normal operation, microprocessor 302 may super-impose internally the first baseline waveform and the second baseline waveform as shown in FIG. 1 to FIG. 3 for creating the superimposed waveform and then instruct the MOS 303 to operate the light source 304 according to the superim-posed waveform. Or alternatively, microprocessor 302 may have the stored data of a periodical waveform as shown by the red waveform in FIG. 1 to FIG. 3 locally (scaled to 40 Hz) and instruct the MOS 303 to operate the light source 304 according to the stored periodical waveform, without doing any superimposition operation of two periodical baseline waveforms.

Figure 7:
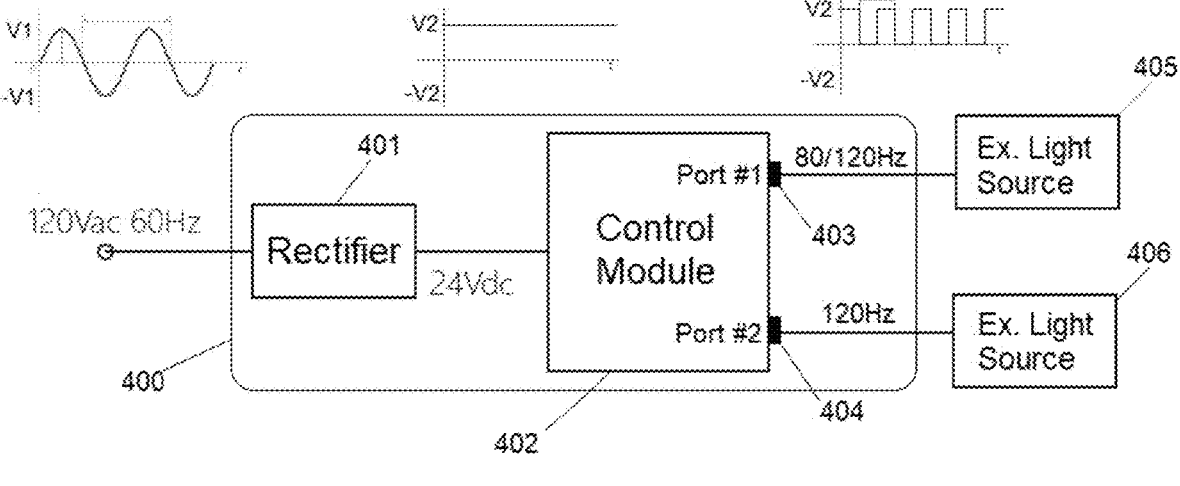
FIG. 7 schematically depicts an embodiment of the present disclosure using one control module with two power output ports supporting recalibration cycle with mono frequency duration.

FIG. 7 shows another embodiment of the gamma stimu-lation apparatus of the present disclosure 400. It comprises a rectifier 401 and a control module 402 having a first power output port 403 and a second power output 404. The rectifier 401 converts an external AC power to an internal DC power (at V2 voltage=24V) to power the control module 402. Embodiment 400 supports a recalibration cycle with mono frequency duration. The control module 402 outputs via the first power output port 403 a first output power having a first periodical waveform (e.g., a square waveform) at a first operating frequency (OF1) either 80 Hz during normal operation (i.e., outside of the mono frequency duration) or 120 Hz during the mono frequency duration. The recalibra-tion cycle may be set between 1 and 120 minutes. The mono frequency duration may be set tween 5 to 60 seconds. The control module 402 outputs via the second power output port 404 a second output power having a second periodical waveform (e.g., a square waveform) at a second operating frequency (OF2) 120 Hz. The first power output port 403 connects and powers a first external light source 405, and the second power output port 404 connects and powers a second external light source 406. A light output of the first external light source 405 and a light output of the second external light source 406 superimpose each other to form a super-imposed light having a superimposed frequency. During normal operation (i.e., outside of the mono frequency dura-tion), the OF1 frequency equals 80 Hz, and thus the super-imposed frequency OF2–OF1=120 Hz–80 Hz=40 Hz. Such superimposed light appears flicker-free (free of flicker) to eyes of a subject. The first periodical waveform and the second periodical waveform have a same waveform style, i.e., square waveform as shown in FIG. 7, but differ in frequency. During the mono frequency duration, the OF1 frequency equals 120 Hz, so the superimposed frequency equals 120 Hz, and there is no flickering, since human subject can't see any flickering at 120 Hz.

In FIG. 7, the first external light source 405 and the second external light source 406 are shown to operate with square waveforms at V2 voltage=24V. However, it is not required for the first external light source 405 and the second external light source 406 to operate at the same 24V DC voltage as the control module 402. The present disclosure only requires that the internal DC power to power the control module and that the first power output port to power the first external light source and the second power output power to power the second external light source. It is foreseeable that the voltage powering the control module may be different from the voltage of the first power output port and/or the voltage of the second power output port.

In another embodiment, control module 402 may be modified to support the mono light source duration such that for every recalibration cycle, the first external light source 405 is turned off during the mono light source duration and at the same time the light output of the second external light source 406 is boosted so as to maintain a total light output of the apparatus the same as when both external light sources are on. Under this embodiment, the first external light source 405 operates at 80 Hz when it is on.

Figure 8:
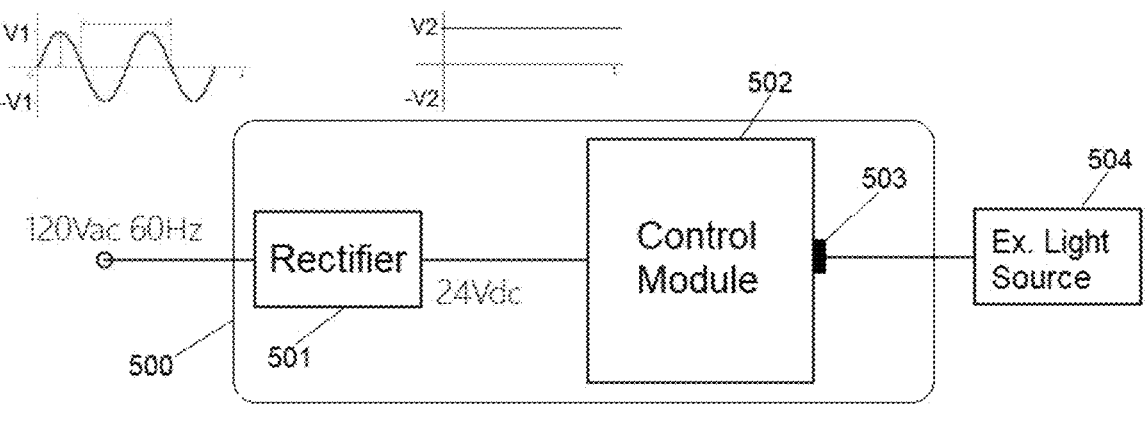
FIG. 8 schematically depicts an embodiment of the present disclosure using one control module with one power output port supporting recalibration cycle the mono frequency duration.

FIG. 8 shows another embodiment of the gamma stimu-lation apparatus of the present disclosure 500. It comprises a rectifier 501 and a control module 502 having a power output port 503. The rectifier 501 converts an external AC power to an internal DC power (at V2 voltage=24V) to power the control module 502. Embodiment 500 supports a recalibration cycle with mono frequency duration. The recalibration cycle may be set between 1 and 120 minutes. The mono frequency duration may be set tween 5 to 60 seconds. During normal operation (i.e., outside of the mono frequency duration), control module 502 outputs via its power output port 503 an output power having a first periodical waveform (e.g., a square waveform) at a first frequency F1 40 Hz. The periodical waveform is decom-posable into a first periodical baseline waveform at a second frequency (F2) 80 Hz (like the first waveform in FIG. 1 but at 80 Hz) and a second periodical baseline waveform at a third frequency (F3) 120 Hz (like the second waveform in FIG. 1 but at 120 Hz) such that F1=F3–F2=120 Hz–80 Hz=40 Hz. The power output port 503 connects and powers an external light source 504. A light output of the external light source 504 appears flicker-free (free of flicker) to the eyes of a subject. Then during the mono frequency duration, control module 502 outputs via its power output port 503 an output power having the second periodical baseline wave-form at the F3 frequency.

In FIG. 8, the external light source 504 may or may not operate at V2 voltage=24V, the voltage used for powering the control module 502. The present disclosure only requires that the internal DC power to power the control module and that the power output port to power an external light source. It is foreseeable that the voltage powering the control module may be different from the voltage of the power output port.

During normal operation, control module 502 may super-impose internally the first baseline waveform and the second baseline waveform as shown in FIG. 1 to FIG. 3 for creating the superimposed waveform. Or alternatively, control mod-ule 502 may have the stored data of a periodical waveform as shown by the red waveform in FIG. 1 to FIG. 3 locally (scaled to 40 Hz) to operate the external light source 504 according to the stored periodical waveform, without doing any superimposition operation of two periodical baseline waveforms.

ADDITIONAL AND ALTERNATIVE IMPLEMENTATION NOTES

Although the techniques have been described in language specific to certain applications, it is to be understood that the appended claims are not necessarily limited to the specific features or applications described herein. Rather, the specific features and examples are disclosed as non-limiting exemplary forms of implementing such techniques.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

What is claimed is:

1. A gamma stimulation apparatus, comprising:
a rectifier;
a control module;
a first modulation operation switch (MOS);
a second MOS;
a first light source; and
a second light source,
wherein:
    the rectifier is configured to convert an external alternating current (AC) power to an internal direct current (DC) power to power the control module, the first light source, and the second light source,
    the control module is configured to send the first MOS a first signal having a first periodical waveform at a first operating frequency (OF1),
    the first MOS is configured to operate the first light source according to the first signal to produce a first light output at the OF1 frequency,
    the control module is configured to send the second MOS a second signal having a second periodical waveform at a second operating frequency (OF2) greater than the OF1 frequency,
    the second MOS is configured to operate the second light source according to the second signal to produce a second light output at the OF2 frequency,
    the first light output and the second light output superimpose each other to form a superimposed light having a superimposed frequency equal to OF2−OF1,
    the superimposed frequency is between 20 Hz and 45 Hz,
    the superimposed light appears flicker-free to eyes of a subject, and
    the control module is configured, for every fixed period of a recalibration cycle, to suspend or turn off one of the first and second light sources for a short period of time of a mono light source duration and to boost a respective light output of the other of the first and second light sources to maintain a total light output of the apparatus to be same as when both the first and second light sources are on.

2. The apparatus of claim 1, wherein the recalibration cycle is between 1 and 120 minutes.

3. The apparatus of claim 1, wherein the mono operating frequency duration is between 5 and 60 seconds.

4. A gamma stimulation apparatus, comprising:
a rectifier;
a control module;
a first modulation operation switch (MOS);
a second MOS;
a first light source; and
a second light source,
wherein:
    the rectifier is configured to convert an external alternating current (AC) power to an internal direct current (DC) power to power the control module, the first light source, and the second light source,
    the control module is configured to send the first MOS a first signal having a first periodical waveform at a first operating frequency (OF1),
    the first MOS is configured to operate the first light source according to the first signal to produce a first light output at the OF1 frequency,
    the control module is configured to send the second MOS a second signal having a second periodical waveform at a second operating frequency (OF2) greater than the OF1 frequency,
    the second MOS is configured to operate the second light source according to the second signal to produce a second light output at the OF2 frequency,
    the first light output and the second light output superimpose each other to form a superimposed light having a superimposed frequency equal to OF2−OF1,
    the superimposed frequency is between 20 Hz and 45 Hz,
    the superimposed light appears flicker-free to eyes of a subject, and
    the control module is configured, for every fixed period of a recalibration cycle, to set the first signal and the second signal at a same frequency for a short period of time of a mono frequency duration.

5. The apparatus of claim 4, wherein the recalibration cycle is between 1 and 120 minutes.

6. The apparatus of claim 4, wherein the mono operating frequency duration is between 5 and 60 seconds.

7. A gamma stimulation apparatus, comprising:
a rectifier;
a first control module;
a second control module;
a first modulation operation switch (MOS);
a second MOS;
a first light source; and
a second light source,
wherein:
    the rectifier is configured to convert an external alternating current (AC) power to an internal direct current (DC) power to power the first control module, the second control module, the first light source, and the second light source,
    the first control module is configured to send the first MOS a first signal having a first periodical waveform at a first operating frequency (OF1),
    the first MOS is configured to operate the first light source according to the first signal to produce a first light output at the OF1 frequency, the second control module is configured to send the second MOS a second signal having a second periodical waveform at a second operating frequency (OF2) greater than the OF1 frequency, the second MOS is configured to operate the second light source according to the second signal to produce a second light output at the OF2 frequency, the first light output and the second light output superimpose each other to form a superimposed light having a superimposed frequency equal to OF2−OF1, the superimposed frequency is between 20 Hz and 45 Hz, the superimposed light appears flicker-free to eyes of a subject, and the first control module and the second control module are configured, for every fixed period of a recalibration cycle, to suspend or turn off one of the first and second light sources for a short period of time of a mono light source duration and to boost a respective light output of the other of the first and second light sources to maintain a total light output of the apparatus to be same as when both the first and second light sources are on.

8. The apparatus of claim 7, wherein the recalibration cycle is between 1 and 120 minutes.

9. The apparatus of claim 7, wherein the mono operating frequency duration is between 5 and 60 seconds.

10. A gamma stimulation apparatus, comprising:
a rectifier;
a first control module;
a second control module;
a first modulation operation switch (MOS);
a second MOS;
a first light source; and
a second light source,
wherein:
  the rectifier is configured to convert an external alternating current (AC) power to an internal direct current (DC) power to power the first control module, the second control module, the first light source, and the second light source,
  the first control module is configured to send the first MOS a first signal having a first periodical waveform at a first operating frequency (OF1),
  the first MOS is configured to operate the first light source according to the first signal to produce a first light output at the OF1 frequency,
  the second control module is configured to send the second MOS a second signal having a second periodical waveform at a second operating frequency (OF2) greater than the OF1 frequency,
  the second MOS is configured to operate the second light source according to the second signal to produce a second light output at the OF2 frequency,
  the first light output and the second light output superimpose each other to form a superimposed light having a superimposed frequency equal to OF2−OF1,
  the superimposed frequency is between 20 Hz and 45 Hz,
  the superimposed light appears flicker-free to eyes of a subject, and
  the first control module and the second control module are configured, for every fixed period of a recalibration cycle, to set the first signal and the second signal respectively at a same frequency for a short period of time of a mono frequency duration.

11. The apparatus of claim 10, wherein the recalibration cycle is between 1 and 120 minutes.

12. The apparatus of claim 10, wherein the mono operating frequency duration is between 5 and 60 seconds.

13. A gamma stimulation apparatus, comprising:
a rectifier;
a control module;
a modulation operation switch (MOS); and
a light source,
wherein:
  the rectifier is configured to convert an external alternating current (AC) power to an internal direct current (DC) power to power the control module and the light source,
  the control module is configured to send the MOS a signal having a periodical waveform signal at a first frequency (F1) between 20 Hz and 45 Hz,
  the MOS is configured to operate the light source according to the signal to produce a light output at the F1 frequency,
  the periodical waveform is decomposable into a first periodical baseline waveform at a second frequency (F2) and a second periodical baseline waveform at a third frequency (F3) such that F1=F3−F2,
  a light output of the light source appears flicker-free to eyes of a subject, and
  the control module is configured, for every fixed period of a recalibration cycle, to operate the MOS according to either the first periodical baseline waveform at the F2 frequency or the second periodical baseline waveform at the F3 frequency for a short period of time of a mono frequency duration.

14. The apparatus of claim 13, wherein the recalibration cycle is between 1 and 120 minutes.

15. The apparatus of claim 13, wherein the mono operating frequency duration is between 5 and 60 seconds.

16. A gamma stimulation apparatus, comprising:
a rectifier; and
a control module having a first power output port and a second power output port,
wherein:
  the rectifier is configured to convert an external alternating current (AC) power to an internal direct current (DC) power to power the control module,
  the control module is configured to output, via the first power output port, a first output power having a first periodical waveform at a first operating frequency (OF1),
  the control module is configured to output, via the second power output port, a second output power having a second periodical waveform at a second operating frequency (OF2),
  the first power output port is configured to power a first external light source to produce a first light output,
  the second power output port is configured to power a second external light source to produce a second light output superimposing the first light output to form a superimposed light having a superimposed frequency equal to OF2−OF1,
  the superimposed frequency is between 20 Hz and 45 Hz,
  the superimposed light appears flicker-free to eyes of a subject, and
  the control module is configured, for every fixed period of a recalibration cycle, to suspend or turn off one of the two output powers for a short period of time of a mono light source duration and to boost the other of the two output powers to maintain a light output to be same as when both of the external light sources are on.

17. The apparatus of claim 16, wherein the recalibration cycle is between 1 and 120 minutes.

18. The apparatus of claim 16, wherein the mono operating frequency duration is between 5 and 60 seconds.

19. A gamma stimulation apparatus, comprising:
a rectifier; and
a control module having a first power output port and a second power output port,
wherein:
    the rectifier is configured to convert an external alternating current (AC) power to an internal direct current (DC) power to power the control module,
    the control module is configured to output, via the first power output port, a first output power having a first periodical waveform at a first operating frequency (OF1),
    the control module is configured to output, via the second power output port, a second output power having a second periodical waveform at a second operating frequency (OF2),
    the first power output port is configured to power a first external light source to produce a first light output,
    the second power output port is configured to power a second external light source to produce a second light output superimposing the first light output to form a superimposed light having a superimposed frequency equal to OF2−OF1,
    the superimposed frequency is between 20 Hz and 45 Hz,
    the superimposed light appears flicker-free to eyes of a subject, and
    the control module is configured, for every fixed period of a recalibration cycle, to output the first output power and the second output power at a same frequency for a short period of time of a mono frequency duration.

20. The apparatus of claim 19, wherein the recalibration cycle is between 1 and 120 minutes.

21. The apparatus of claim 19, wherein the mono operating frequency duration is between 5 and 60 seconds.

22. A gamma stimulation apparatus, comprising:
a rectifier; and
a control module having a power output port,
wherein:
    the rectifier is configured to convert an external alternating current (AC) power to an internal direct current (DC) power to power the control module,
    the control module is configured to output, via the power output port, an output power having a periodical waveform signal at a first frequency (F1) between 20 Hz and 45 Hz,
    the periodical waveform is decomposable into a first periodical baseline waveform at a second frequency (F2) and a second periodical baseline waveform at a third frequency (F3) such that F1=F3−F2,
    the power output port is configured to power an external light source to produce a light output of the external light source appears flicker-free to eyes of a subject, and
    the control module is configured, for every fixed period of a recalibration cycle, to output the output power according to either first periodical baseline waveform at the F2 frequency or the second periodical baseline waveform at the F3 frequency for a short period of time of a mono frequency duration.

23. The apparatus of claim 22, wherein the recalibration cycle is between 1 and 120 minutes.

24. The apparatus of claim 22, wherein the mono operating frequency duration is between 5 and 60 seconds.

* * * * *